US00PP16283P3

(12) United States Plant Patent
Bernuetz

(10) Patent No.: US PP16,283 P3
(45) Date of Patent: Feb. 21, 2006

(54) ***ARGYRANTHEMUM* PLANT NAMED 'OHAR01245'**

(50) Latin Name: *Argyranthemum×hybrida*
Varietal Denomination: OHAR01245

(75) Inventor: Andrew Bernuetz, Silverdale (AU)

(73) Assignee: Bonza Botanicals Pty., Ltd., Sydney (AU)

( * ) Notice: Subject to any disclaimer, the term of this patent is extended or adjusted under 35 U.S.C. 154(b) by 84 days.

(21) Appl. No.: 10/741,695

(22) Filed: Dec. 19, 2003

(65) Prior Publication Data

US 2005/0138712 P1 Jun. 23, 2005

(51) Int. Cl.
*A01H 5/00* (2006.01)

(52) U.S. Cl. ..... Plt./263

(58) Field of Classification Search ..... Plt./263
See application file for complete search history.

*Primary Examiner*—Anne Marie Grunberg
*Assistant Examiner*—June Hwu
(74) *Attorney, Agent, or Firm*—Burns, Doane, Swecker & Mathis, L.L.P.

(57) ABSTRACT

A new and distinct cultivar of *Argyranthemum* plant named 'OHAR01245' characterized by its double inflorescence form with pink-colored ray florets and purple/yellow bi-colored disc florets, freely branching character, medium green-colored foliage and compact upright growth habit.

1 Drawing Sheet

Latin name of the genus and species of plant claimed: *Argyranthemum×hybrida*.
Variety denomination: 'OHAR01245'.

BACKGROUND OF THE INVENTION

The present invention relates to a new and distinct cultivar of *Argyranthemum* plant botanically known as *Argyranthemum×hybrida* and hereinafter referred to by the cultivar name 'OHAR01245'.

The new *Argyranthemum* originated in a controlled breeding program in Winmalee, New South Wales, Australia during February 2001. The objectives of the breeding program were the development of *Argyranthemum* plants that are freely branching, have a compact upright growth habit are freely flowering and have unique flower coloration.

The female (seed) parent of the new cultivar was the *Argyranthemum* variety 'Cobeer' (U.S. Plant Pat. No. 14,174) characterized by its fully double inflorescence form, pink-colored ray florets, compact growth habit, and dark green foliage. The male (pollen) parent of the new cultivar was the *Argyranthemum* cultivar 'Pink Annabel' (not patented) characterized by its single inflorescence form, dark pink-colored ray florets, and medium open growth habit. Seed from the above stated cross-pollination was germinated and grown to maturity. One plant from within the progeny was discovered and selected by the inventor during October 2001, in a controlled environment at Winmalee, New South Wales, Australia.

Asexual reproduction of the new cultivar by terminal stem cuttings since October 2001 at Winmalee, NSW, Australia and West Chicago, Ill. has demonstrated that the new cultivar reproduces true to type with all the characteristics as herein described, firmly fixed and retained through successive generations of such asexual propagation.

SUMMARY OF THE INVENTION

The new cultivar has not been observed under all possible environmental conditions to date. Accordingly, it is possible that the phenotype may vary somewhat with variations in the environment, such as temperature, light intensity, and day length without, however, any variance in genotype.

It was repeatedly found that the cultivar of the present invention:

1. Exhibits a double inflorescence form with pink-colored ray florets and purple/yellow bi-colored disc florets,
2. Forms medium green-colored foliage,
3. Exhibits a freely branching character, and
4. Exhibits a compact upright growth habit.

Plants of the new cultivar differ from plants of the female parent primarily in inflorescence size and foliage color, and from plants of the male parent primarily in flower form and growth habit.

Plants of the new cultivar are most similar to the cultivar 'Summer Melody' (U.S. Plant Pat. No. 11,763). However, in side-by-side comparisons, plants of the new cultivar differ from plants of 'Summer Melody' in the following characteristics:

1. Plants of the new cultivar have larger inflorescences than plants of 'Summer Melody',
2. Plants of the new cultivar have larger leaves than plants of 'Summer Melody', and
3. Plants of the new cultivar have more disc florets than plants of 'Summer Melody'.

BRIEF DESCRIPTION OF THE PHOTOGRAPHS

The accompanying photographs show as nearly true as it is reasonably possible to make the same in color illustrations of this type, typical flower and foliage characteristics of the new cultivar. Colors in the photographs differ slightly from the color values cited in the detailed description which more accurately describe the colors of the new cultivar. The plants were grown in 10 m cm pots for 10 weeks in a greenhouse at West Chicago, Ill.

DETAILED BOTANICAL DESCRIPTION

Figure 1:
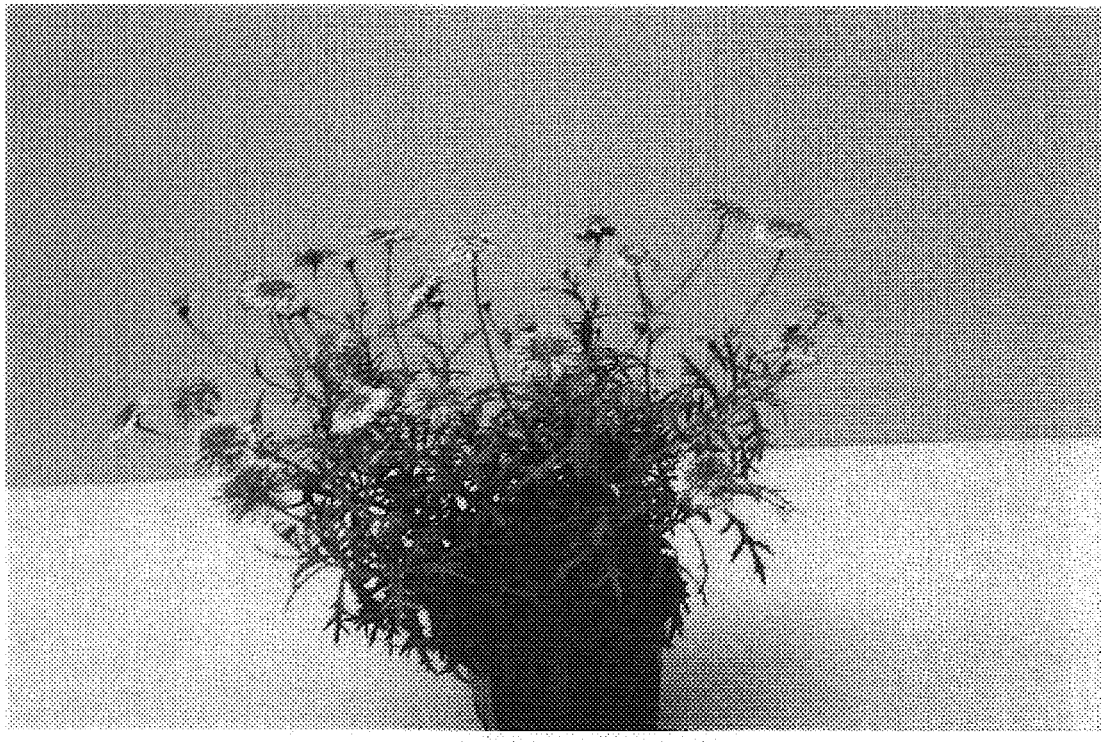
FIG. 1 illustrates a side view of the overall growth and flowering habit of the new cultivar.
Figure 2:
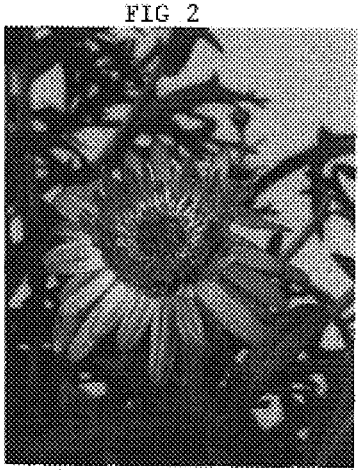
FIG. 2 illustrates a close-up view of an individual flower of the new cultivar when just opening.
Figure 3:
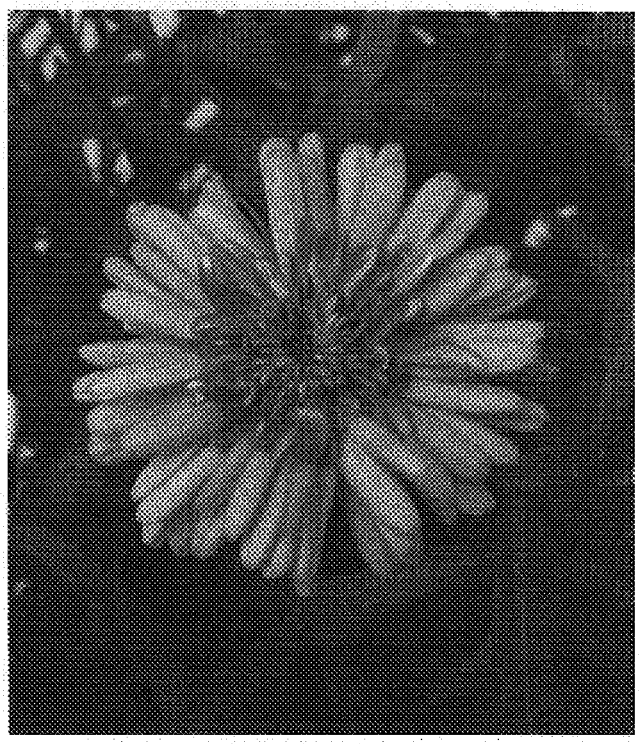
FIG. 3 illustrates a close-up view of an individual flower of the new cultivar with ray florets fully open.

The chart used in the identification of colors described herein is The R.H.S. Colour Chart of The Royal Horticultural Society, London, England, 1995 edition, except where color terms of ordinary significance are used. The color values were determined on Sep. 25, 2003. The readings were taken between 1:00 and 3:00 p.m. under natural light conditions. The plants were produced from cuttings taken from stock plants and grown in a double polycarbonate-covered greenhouse under conditions comparable to those used in commercial practice. The plants were grown in 10 cm pots for 10 weeks while utilizing a soilless growth medium. Greenhouse temperatures were maintained at approximately 65°–78° F. (18°–25° C.) during the day and approximately 50°–60° F. (10°–15° C.) during the night. Greenhouse light levels were maintained at approximately 6,000–9,000 foot-candles during the day.

Botanical classification: *Argyranthemum×hybrida* cultivar 'OHAR01245'.

Parentage:

*Female (seed) parent.*—*Argyranthemum* cultivar 'Cobeer' (U.S. Plant Pat. No. 14,174).

*Male (pollen) parent.*—*Argyranthemum* cultivar 'Pink Annabel' (not patented).

Propagation:

*Type cutting.*—Terminal stem.

*Time to initiate roots.*—Approximately 7 to 10 days.

*Time to produce a rooted cutting.*—Approximately 14 to 21 days.

*Root description.*—Fine, fibrous.

*Rooting habit.*—Freely branching.

Plant description:

*Crop time.*—Approximately 8 weeks in a 10 cm pot.

*Habit of growth.*—Compact. Freely branching. One or two pinches improves basal branching.

*Form.*—Upright, mounded.

*Plant height.*—A mature plant, 10 weeks after the planting of a rooted cutting, commonly measures approximately 25.3 cm from soil level to top of plant plane.

*Plant width (area of spread).*—Approximately 34.3 cm.

*Branch description.*—Quantity per plant: Primary: 14. Texture: Glabrous. Length from soil level to base of peduncle: Approximately 18.1 cm. Diameter: Approximately 2.6 mm. Internode length at middle of branch: Approximately 7.9 mm. Color: 144A.

*Foliage description.*—Leaves are simple and non-fragrant. Arrangement: Alternate. Quantity per branch: Approximately 23. Aspect: At an acute angle to the stem. Shape: Pinnatified. Margin: Entire. Apex: Acute. Base: Sessile, clasping. Texture: Upper and lower surfaces are glabrous. Venation pattern: Pinnate. Length: Approximately 6.5 cm. Width: Approximately 2.3 cm. Color of mature foliage: Upper surface: 137A with venation of 137D. Lower surface: 137B with venation of 137D.

Flowering description:

*Flowering habit.*—Freely flowering.

*Natural flowering season.*—Year round in greenhouse environment and spring through autumn in outdoor garden.

Inflorescence description:

*Appearance.*—Solitary, composite. Persistent. Shape: Round. Aspect: Facing upward or outward. Disc and ray florets develop acropetally on a capitulum. Fragrance: None. Quantity of flowers and buds per branch: Approximately 3 flowers and 3 buds.

*Size.*—Diameter: Approximately 3.4 cm. Depth: Approximately 1.1 cm.

*Lastingness of inflorescence.*—Approximately 7–10 days.

*Bud.*—Shape: Round, flat. Diameter: Approximately 6 mm. Depth: Approximately 7 mm. Color: 165B.

*Ray florets.*—Quantity per inflorescence: Approximately 112, arranged in a several whorls. Aspect: Flat to slightly concave. Arrangement: Very slightly overlapping. Shape: Ligulate. Margin: Entire. Apex: Emarginate. Base: Attenuate and fused to form tube. Texture: Glabrous and ribbed. Florets in outermost whorl: Length: Approximately 2.2 cm. Width: Approximately 5 mm. Color of upper surface: N74D with some coloration of 155D at the base. Color of lower surface: N74D. Florets in innermost whorl: Length: 8 mm. Width: 4 mm. Color of upper surface: N74B. Color of lower surface: 75D. Tube texture: Pubescent. Tube color: 145B.

*Disc.*—Diameter: Approximately 8 mm. Depth: Approximately 1 cm.

*Disc florets.*—Quantity per inflorescence: Approximately 32. Shape: Tubular, salverform with five lobes each having an acute apex. Margin: Entire. Texture: Glabrous. Length: Approximately 8 mm. Diameter at apex: Approximately 3 mm. Diameter at base: Approximately 1 mm. Color: 13A with 71A at tips of each lobe. Calyx: Shape: tubular. Length: Approximately 2 mm. Diameter: Approximately 1 mm. Color: Colorless, translucent.

*Phyllaries.*—Quantity per inflorescence: Approximately 8. Arrangement: Imbricate. Shape: Ovate. Apex: Acute. Base: Truncate. Margin: Entire. Texture: Glabrous. Length: Approximately 7 mm. Width: Approximately 3 mm. Color of upper surface: Closest to 145C. Color of lower surface: Closest to 145D in center, 165B/C at edges.

*Peduncle.*—Strength: Strong. Texture: Glabrous. Aspect: At an acute angle to the stem. Length: Approximately 8.4 cm. Diameter: Approximately 1 mm. Color: 144A.

*Reproductive organs.*—Androecium: Present on disc florets only. Stamens: 5 fused to form tube around pistil. Anther shape: Linear. Anther length: Less than 1 mm. Anther color: N163C. Amount of pollen: Abundant. Pollen color: 17A. Gynoecium: Present on ray and disc florets. There is one pistil per floret. Pistil length: 4 mm. Stigma shape: Two parted. Stigma length: 1 mm. Stigma color: 13A. Style length: 2 mm. Style color: 144C. Ovary color: 144C.

Seed and fruit production: Neither seed nor fruit production has been observed.

Disease and pest resistance: Resistance to pathogens and pests common to *Argyranthemums* has not been observed.

Hardiness zone: 'OHAR01245' is hardy in zones nine (9) and above.

What is claimed is:

1. A new and distinct cultivar of *Argyranthemum* plant named 'OHAR01245' substantially as herein shown and described, which:

1. Exhibits a double inflorescence form with pink-colored ray florets and purple/yellow bi-colored disc florets,
2. Forms medium green-colored foliage,
3. Exhibits a freely branching character, and
4. Exhibits a compact upright growth habit.

* * * * *